United States Patent [19]

Riegel et al.

[11] 4,329,525
[45] * May 11, 1982

[54] PRODUCTION OF CHLORINATED COMPOUNDS BY USE OF MOLTEN SALTS

[75] Inventors: Herbert Riegel, Maplewood; Vincent Strangio, Glen Ridge; Morgan C. Sze, Upper Montclair, all of N.J.

[73] Assignee: The Lummus Company, Bloomfield, N.J.

[*] Notice: The portion of the term of this patent subsequent to Oct. 10, 1995, has been disclaimed.

[21] Appl. No.: 879,802

[22] Filed: Feb. 21, 1978

[51] Int. Cl.³ .............................................. C07C 17/00
[52] U.S. Cl. .................... 570/191; 570/192; 570/196; 570/200; 570/207; 570/216; 570/219; 570/231; 570/234; 570/252
[58] Field of Search ........... 260/656 R, 654 R, 654 H, 260/662 R, 649 R; 570/191, 192, 196, 200, 207, 216, 219, 231, 234, 252

[56] References Cited

U.S. PATENT DOCUMENTS

| | | | |
|---|---|---|---|
| 2,418,931 | 4/1947 | Gorin | 260/DIG. 42 |
| 2,498,552 | 2/1950 | Kilgren et al. | 260/DIG. 42 |
| 3,363,010 | 1/1968 | Schwarzenbek | 260/649 R |
| 3,671,596 | 6/1972 | Bellis | 260/656 R |
| 3,872,174 | 3/1975 | Bellis | 260/656 R |
| 3,937,744 | 2/1976 | Riegel | 260/656 R |
| 4,046,823 | 9/1977 | Gordon et al. | 260/662 R |

Primary Examiner—Delbert E. Gantz
Assistant Examiner—Joseph A. Boska
Attorney, Agent, or Firm—Louis E. Marn; Elliot M. Olstein

[57] ABSTRACT

A compound is chlorinated with chlorine to produce chlorinated product and hydrogen chloride byproduct. Recovered hydrogen chloride byproduct is contacted with oxygen and a molten salt mixture containing the higher and lower valent chlorides of a multivalent metal, such as cuprous and cupric chloride, to effect recovery of the hydrogen chloride by enriching the molten salt content of the higher valent chloride. The molten salt, enriched in higher valent chloride, is then dechlorinated by use of a stripping gas, preferably hydrogen chloride, to produce a gaseous effluent containing stripped chlorine and the stripping gas, which is then recycled to the chlorination step. The presence of stripping gas, as a diluent, improves the chlorination operation.

13 Claims, 1 Drawing Figure

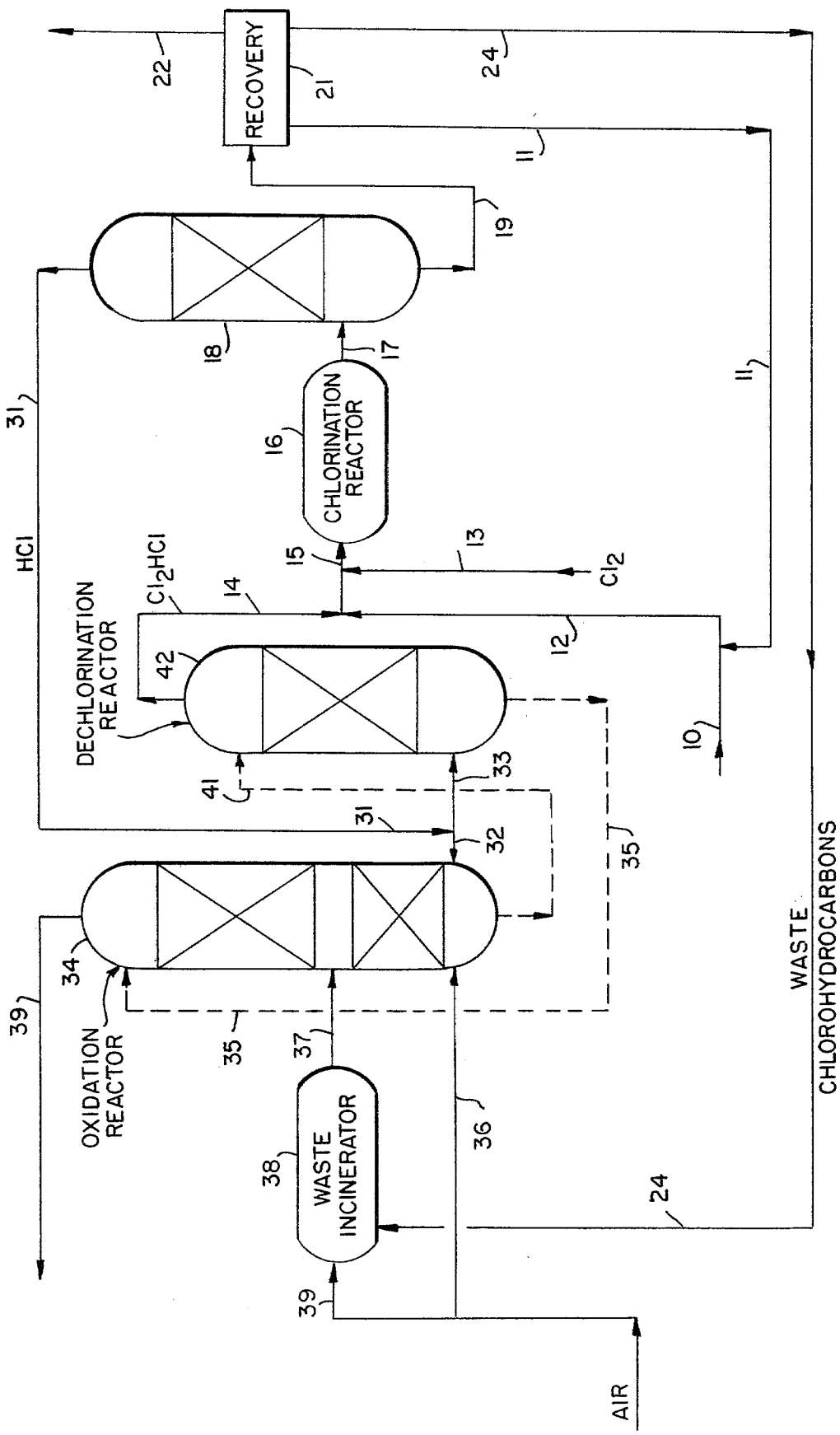

PRODUCTION OF CHLORINATED COMPOUNDS BY USE OF MOLTEN SALTS

This invention relates to the production of chlorinated compounds, and more particularly to the production of chlorinated compounds by the use of molten salts.

Molten salt mixtures, containing the higher and lower valent chlorides of a multivalent metal have been previously employed for the production of chlorinated hydrocarbons. Thus, for example, U.S. Pat. No. 3,879,482 describes a process for producing vinyl chloride wherein ethane and/or ethylene is contacted with a molten salt mixture containing the higher and lower valent chlorides of a multivalent metal, such as cuprous and cupric chloride, and hydrogen chloride and/or chlorine to produce an effluent containing vinyl chloride.

Similarly, U.S. Pat. No. 3,865,886 describes a process for the production of allyl chloride employing a molten salt mixture containing the higher and lower valent chlorides of a multivalent metal. In this process, propane is contacted with hydrogen chloride and/or chlorine and the molten salt mixture to produce an effluent containing allyl chloride.

The present invention is directed to the production of chlorinated compounds, by the use of molten salts, without direct contact between the fresh feed and the molten salt.

In accordance with the present invention, there is provided a process for chlorinating a compound wherein the compound is contacted with chlorine to produce an effluent containing chlorinated product and hydrogen chloride. The chlorinated product and hydrogen chloride are recovered from the effluent, with at least a portion of the recovered hydrogen chloride being contacted in an oxidation zone with gaseous oxygen and a molten salt mixture containing the higher and lower valent chlorides of a multivalent metal to effect recovery of hydrogen chloride by enriching the higher valent chloride content of the molten salt. The molten salt, now enriched in higher valent metal chloride, is then passed to a dechlorination zone wherein the molten salt is dechlorinated with the use of a stripping gas to effect stripping of chlorine from the molten salt. Chlorine, recovered from the dechlorination, is then passed to the chlorination step. In this manner, an organic compound is chlorinated by the use of chlorine, with hydrogen chloride byproduct being ultimately recovered and reconverted to chlorine for use in the chlorination, whereby fresh chlorine feed is effectively utilized for the production of chlorinated product.

The molten salts employed in the present invention include the higher and lower valent forms of a chloride of a multivalent metal; i.e., a metal having more than one positive valent state, such as manganese, iron, copper, cobalt and chromium, preferably copper. In the case of higher melting multivalent metal chlorides, such as copper chlorides, a metal salt melting point depressant, which is non-volatile and resistant to the action of oxygen at the processing conditions, such as a chloride of a univalent metal; i.e., a metal having only one positive valent state, is added to the multivalent metal chloride to form a molten salt mixture having a reduced melting point. The metal chlorides employed as melting point depressants are preferably alkali metal chlorides, such as potassium and lithium chloride, in particular, but it is to be understood that other metal chlorides and mixtures thereof, such as the heavy metal chlorides; i.e., heavier than copper, of groups I, II, and III and IV of the Periodic Table; e.g., zinc, silver and thallium chloride, may also be employed. The metal chloride melting point depressant is added in an amount sufficient to maintain the salt mixture as a melt at the reaction temperatures, and is generally added in an amount sufficient to adjust the melting point of the molten salt mixture to a temperature of below about 500° F. In the case of the salt mixture of copper chlorides and potassuim chloride, the composition of the melt generally ranges from about 15% to about 40%, preferably about 20% to 25%, by weight, potassium chloride with the remainder being copper chlorides. It is to be understood, however, that in some cases the molten salt mixture may have a melting point higher than 500° F., provided that the mixture remains in the form of the melt throughout the processing steps. It is further to be understood that the melt may contain a mixture of multivalent metal chlorides or other reaction promoters.

As hereinabove indicated, hydrogen chloride byproduct produced during the chlorination reaction is converted to chlorine for recycle to the chlorination step by the use of the molten salt, with such conversion being effected in two reaction zones. In particular, the hydrogen chloride byproduct is contacted with gaseous oxygen and the molten salt containing the higher and lower valent chlorides of the multivalent metal in an oxidation reaction zone to effect conversion and recovery of hydrogen chloride by enriching the higher valent metal chloride content of the molten salt.

The oxidation reaction zone is generally operated at a pressure of from about 1 atm to about 20 atm, and preferably at a pressure of from about 3 atm to about 6 atm. The salt inlet temperature to the oxidation reaction zone is generally from about 750° F. to about 950° F. and preferably from about 770° F. to about 840° F.

The oxidation reaction zone is provided with gaseous oxygen (either as oxygen alone, or in admixture with another gas, for example, preferably air), in an amount sufficient to effect oxidation of the hydrogen chloride to effect recovery thereof by enriching the higher valent chloride content of the salt. The precise amount of oxygen required for effecting such conversion can be readily determined by those skilled in the art from the teachings herein. The oxygen is preferably employed in an amount whereby the molten salt withdrawn from the oxidation reaction zone is free of oxychloride. The oxidation reaction for effecting recovery of hydrogen chloride, employing copper chloride as a representative multivalent metal chloride, is represented by the following equations:

$$2CuCl + \tfrac{1}{2}O_2 \rightarrow CuCl_2 \cdot CuO \tag{1}$$

$$CuCl_2 \cdot CuO + 2HCl \rightarrow 2CuCl_2 + H_2O \tag{2}$$

$$2CuCl + \tfrac{1}{2}O_2 + 2HCl \rightarrow 2CuCl_2 + H_2O \tag{3}$$

The molten salt mixture from the oxidation reaction zone, which is now enriched in the higher valent metal chloride, preferably cupric chloride, and which is also preferably free of oxychloride, is then introduced into the dechlorination reaction zone wherein chlorine is stripped from the salt employing a stripping gas to facilitate such chlorine stripping. The dechlorination reaction zone is generally operated at a pressure of from about 0.1 atm to about 3 atm, and preferably a pressure of from about 1 atm to about 2 atm. The molten salt inlet temperature to the dechlorination reaction zone is generally from about 850° F. to about 1000° F., and preferably from about 900° F. to about 950° F. The dechlorination reaction zone is further provided with a stripping gas in an amount sufficient to facilitate stripping of chlorine from the molten salt. The amount of stripping gas employed is determined by the amount of chlorine desired in the dechlorination reactor effluent. The moles of stripping gas per mole of chlorine is then:

Total Pressure less Chlorine Partial Pressure / Chlorine Partial Pressure

The conditions of the dechlorination and the amount of stripping gas provided are generally coordinated to provide a dechlorination effluent containing from 5 to 40 mole percent of chlorine.

The stripping gas employed for stripping chlorine from the molten salt is one which is inert with respect to the molten salt, and which is also preferably inert with respect to the subsequent chlorination reaction in that in accordance with the preferred embodiment, chlorine produced in the dechlorination is not separated from the stripping gas and is employed directly for the chlorination operation. As respresentative examples of suitable stripping gases, there may be mentioned: hydrogen chloride, nitrogen, helium, carbon dioxide, etc. The preferred stripping gas is hydrogen chloride in that hydrogen chloride is readily available in the process. The stripping of chlorine from the molten salt, employing copper chlorides as representative multivalent metal chlorides, is represented by the following equation:

$$2CuCl_2 \rightarrow 2CuCl + Cl_2 \quad (4)$$

In accordance with a preferred embodiment of the present invention, the operating pressure of the oxidation reaction zone is at least 0.5 atm. greater than the operating pressure of the dechlorination reaction zone, with the pressure of the oxidation reaction zone generally being in the order of from about 1 atm. to about 10 atm. greater than the pressure in the dechlorination reaction zone. In addition, the salt inlet temperature to the oxidation reactor is generally at least 50° F. less than the inlet temperature to the dechlorination reactor, with the salt inlet temperature to the oxidation reactor generally being from 80° F. to 150° F. less than the salt inlet temperature to the dechlorination reactor. The change in conditions between the oxidation reaction zone and the dechlorination reaction zone increases chlorine yields based on hydrogen chloride introduced into the oxidation reaction zone. The temperature change and change in the higher valent chloride concentration between the oxidation and dechlorination reaction zones can be achieved, without the use of heat exchange apparatus, by controlling the salt circulation rate. In general, the salt circulation rate is in the order of from about 20 to about 300 moles salt/mole $Cl_2$ stripped and preferably from about 40 to about 90 moles salt/mole $Cl_2$ stripped.

In accordance with a preferred embodiment, the dechlorination reaction zone is maintained dry in order to provide a dechlorination effluent which avoids the presence of aqueous hydrogen chloride, and the necessity to separate large amounts of water from the chlorination effluent. The dechlorination reaction zone may be maintained in a dry state by introducing a dry stripping gas, and by preventing water from being present in the molten salt withdrawn from the oxidation reaction zone. The molten salt withdrawn from the oxidation reaction zone may be maintained in a dry state by contacting the salt, immediately prior to withdrawal thereof from the oxidation reaction zone with hydrogen chloride feed to strip water therefrom. The hydrogen chloride also converts any copper oxide present in the salt whereby the salt introduced into the dechlorination zone is free of both water and copper oxide.

In accordance with a preferred embodiment, the chlorine containing effluent withdrawn from the dechlorination reactor is employed without further treatment in the chlorination, except in some cases for separating any entrained and vaporized salt. The use of the dechlorination effluent, which includes chlorine and stripping gas, directly, offers the advantage that there is a savings in heat and processing equipment costs. In addition, the stripping gas present in the chlorine functions as a diluent in the chlorination reaction which aids in stabilizing and controlling the chlorination reaction temperature. It is also possible, however, if necessary to treat the dechlorination effluent to separate the stripping gas from the chlorine, whereby chlorine, in the essential absence of stripping gas, is recycled to the chlorination reaction. It is also possible to effect compression of the stream and/or heating or cooling thereof, as appropriate, for subsequent chlorination. The use of the stripping gas as a diluent for the chlorination is preferred in that it affords good temperature control to both improve yield and increase onstream time.

The chlorine generated from the byproduct hydrogen chloride, as well as fresh feed chlorine and organic compound to be chlorinated are introduced into a chlorination reaction zone in order to effect chlorination to produce chlorinated product, as well as hydrogen chloride byproduct. The chlorination reaction may be any one of a wide variety of chlorination reactions to produce chlorinated products. Thus, for example, the chlorination may be the chlorination of a hydrocarbon or a partially chlorinated derivative thereof, which can be an aliphatic hydrocarbon, both saturated and olefinically unsaturated, a cycloaliphatic hydrocarbon, both saturated and olefinically unsaturated, or an aromatic hydrocarbon. As representative examples of such feeds, there may be mentioned: alkanes having from 1–10 carbon atoms, alkenes having from 1–10 carbon atoms, dienes having from 3–10 carbon atoms, cycloalkanes having from 5–12 carbon atoms, cycloalkenes having from 5–12 carbon atoms, cycloalkadienes having from 5–12 carbon atoms, benzene unsubstituted or substituted with one or more alkyl or alkenyl groups, and the like, and the partially chlorinated derivatives thereof.

The chlorination of the organic hydrocarbon can be effected at chlorination conditions which are generally known in the art. The specific details for effecting the chlorination of a specific organic form no part of the present invention, and as a result, no further teachings in this respect are deemed necessary for a clear understanding of the present invention in that the manner of effecting chlorination of various organic compounds is well known in the art. In general, such chlorination is effected at a temperature in the order of from about 0° F. to about 1100° F., and at a pressure of from about 0.1 atm to about 20 atm. As known in the art, such chlorination is generally effected in the presence of a suitable chlorination catalyst. As representative examples of such suitable chlorination catalysts, there may be mentioned: the chlorides of zinc, copper, iron, cobalt, nickel, rare earth metals, etc. In some cases, chlorination can be effected in the absence of a catalyst, or as known in the art, by the use of ultraviolet light.

The invention will be further described with respect to an embodiment thereof illustrated in the accompanying drawing, wherein:

The drawing is a simplified schematic flow diagram of an embodiment of the present invention.

It is to be understood, however, that the scope of the invention is not to be limited to the hereinafter described specific embodiment.

Referring now to the drawing, fresh feed organic compound to be chlorinated, in line 10, is combined with recycle unreacted feed organic compound in line 11 and the combined stream in line 12 is combined with fresh feed chlorine in line 13 and a dechlorination reaction effluent in line 14, containing chlorine and hydrogen chloride, and obtained as hereinafter described. The combined stream in line 15 is introduced into a chlorination reactor, schematically generally indicated as 16.

In chlorination reactor 16, the organic feed is chlorinated by direct contact with chlorine to produce chlorinated product and hydrogen chloride byproduct. The hydrogen chloride introduced with the feed does not react in the chlorine reactor. A chlorination reaction effluent, containing chlorinated product, hydrogen chloride byproduct, as well as unreacted feed and other byproducts, is withdrawn from reactor 16 through line 17 and introduced into a distillation column, schematically generally indicated as 18. The distillation column 18 is operated in a manner such as to recover hydrogen chloride, as overhead, with the hydrogen chloride being essentially free of organics. The operation of such a fractional distillation column in order to effect recovery of gaseous hydrogen chloride from the remainder of the reaction effluent is deemed to be well within the scope of those skilled in the art from the teachings herein. It is also to be understood that such separation of hydrogen chloride could be effected by other known techniques and, accordingly, the present invention is not limited to the disclosed fractional distillation.

An organic bottoms, essentially free of hydrogen chloride is withdrawn from column 18 through line 19. The organic product in line 19 is introduced into a separation and recovery section schematically generally indicated as 21 in order to recover reaction product, organic byproducts, and recycle for the chlorination reactor. Thus, the final product is recovered through line 22, and unreacted feed is recovered through line 11 for recycle to the chlorination reactor 16. Organic byproducts are recovered through line 23, and such byproducts, if any, can be separately marketed, employed as feed for the production of other products, or if potentially convertible to the final chlorinated product, such byproducts can be recycled to the chlorination reactor 16 or to another reactor for producing additional final product.

Chlorinated hydrocarbons which are not potentially maketable, or which are not suitable for the production of desired product can be recovered through line 24 for treatment as hereinafter described.

The hydrogen chloride recovered from tower 18 in line 31 is split into two portions, one portion of which is the net hydrogen chloride produced in the chlorination reactor 16, in line 32, and the other portion, in line 33, being the portion employed as stripping gas for the dechlorination reactor, which is ultimately introduced into the chlorination reactor 16. The net hydrogen chloride in line 32 is introduced into an oxidation reactor, schematically indicated as 34 for effecting recovery thereof.

The oxidation reactor 34 is provided through line 35 with a molten salt mixture, containing the higher and lower valent chlorides of a multivalent metal, and further including a melting point depressant, such as a mixture of cuprous chloride, cupric chloride and potassium chloride, and is further provided with an oxygen containing gas, such as air, through line 36.

A chlorinated hydrocarbon combustion effluent, containing hydrogen chloride and/or chlorine is also introduced into reactor 34 through line 37. Such effluent is obtained by burning the waste chlorinated byproducts in line 24 in a combustion zone 38 which is provided with air through line 39.

As a result of the contact between the hydrogen chloride, air and molten salt, the hydrogen chloride is recovered by enriching the cupric chloride content of the molten salt. In addition, any gaseous chlorine present in the effluent in line 37 is recovered by enriching the cupric chloride content of the molten salt.

A gaseous effluent is withdrawn from reactor 34 through line 39, and such gaseous effluent may include equilibrium amounts of hydrogen chloride, and chlorine, if any, as well as components introduced with the combustion effluent in line 37, such as carbon oxides, and with the air, such as nitrogen. The effluent in line 39 may be further treated, as known in the art, in order to recover hydrogen chloride for recycle to the oxidation reactor 34. Thus, for example, such effluent in line 39 may be further treated as described in U.S. Pat. No. 3,968,200.

A molten salt, now enriched in cupric chloride, is withdrawn from reactor 34 through line 41 and introduced into the top of a dechlorination reactor, schematically generally indicated as 42. The dechlorination reactor 42 is operated as hereinabove described in order to strip chlorine from the salt. The dechlorination reactor is provided with hydrogen chloride stripping gas through line 33, and as a result of the conditions in reactor 42 and the stripping action of the hydrogen chloride, gaseous chlorine is stripped from the salt, with the cupric chloride being converted to cuprous chloride, Molten salt withdrawn from reactor 42 is recycled to reactor 34 through line 35.

A dechlorination effluent, containing gaseous chlorine, as well as hydrogen chloride, introduced as stripping gas, is withdrawn from reactor 42 through line 14, for introduction into the chlorination reactor 16. The chlorine stripped from the salt is that produced from the hydrogen chloride generated in reactor 16, as well as any chlorine values recovered from waste chlorinated product produced in the chlorination reactor 16.

As hereinabove described, the mixture of chlorine and hydrogen chloride stripping gas is preferably directly employed for the chlorination reaction; however, the effluent from the dechlorination reactor 42 may be treated to separately recover the chlorine for introduction into the chlorination reactor 16.

In addition, although the addition of hydrogen chloride as the stripping gas is preferred, the stripping of chlorine from the molten salt may be effected by the use of a stripping gas other than hydrogen chloride, e.g., nitrogen.

The above modifications and others should be apparent to those skilled in the art from the teachings herein.

The present invention is particularly advantageous in that it permits chlorination with effective recovery of hydrogen chloride byproduct for use in the chlorination. In addition, the use of recovered chlorine diluted with the stripping gas provides for improved temperature control, which improves selectivity. In addition, chlorine does not have to be precisely metered to the chlorinator to avoid chlorinolysis and the resultant product of carbon, tars and byproducts. Thus, a more stable operation is achieved. Furthermore, the sensible heat of the dechlorination effluent can be recovered in the chlorinator.

What is claimed is:

1. A process for chlorinating a compound which is either a hydrocarbon or partially chlorinated hydrocarbon, comprising:
   (a) contacting in a chlorination zone said (a) compound with fresh feed chlorine and a recycle mixture containing chlorine and hydrogen chloride to produce an effluent containing chlorinated product and hydrogen chloride;
   (b) recovering chlorinated product and hydrogen chloride;
   (c) introducing a first portion of recovered hydrogen chloride into an oxidation reaction zone wherein the hydrogen chloride is contacted with a molten salt mixture containing the higher and lower valent chlorides of a multivalent metal and oxygen to recover chlorine by enriching the higher valent metal chloride content of the molten salt;
   (d) passing molten salt from the oxidation reaction zone to a dechlorination zone wherein the molten salt is contacted with a second portion of recovered hydrogen chloride, as stripping gas, to strip chlorine from the molten salt; and
   (e) withdrawing from the dechlorination zone a mixture of chlorine and hydrogen chloride for introduction into the chlorination zone as said recycle mixture.

2. The process of claim 1 wherein the molten salt mixture contains a mixture of cuprous and cupric chloride.

3. The process of claim 2 wherein the gaseous chlorine and stripping gas recovered from the dechlorination zone contains from 5 to 40 mole percent chlorine.

4. The process of claim 3 wherein the oxidation reaction zone is operated at a pressure of from 1 to 20 atm and a molten salt inlet temperature of from 750° F. to 950° F. and the dechlorination zone is operated at a pressure from 0.1 to 3.0 atm, and a molten salt inlet temperature of from 850° F. to 1000° F.

5. The process of claim 4 wherein the oxidation reaction zone pressure is at least 0.5 atm greater than the dechlorination zone pressure and the molten salt inlet temperature to the oxidation reaction zone is at least 50° F. less than the molten salt inlet temperature to the dechlorination zone.

6. The process of claim 5 wherein the molten salt mixture introduced into the dechlorination zone is free of water and copper oxide.

7. A process for chlorinating a compound which is either a hydrocarbon or partially chlorinated hydrocarbon, comprising:
   (a) contacting in a chlorination zone said compound with chlorine to produce an effluent containing chlorinated product and hydrogen chloride;
   (b) recovering chlorinated product and hydrogen chloride;
   (c) introducing at least a portion of the recovered hydrogen chloride into an oxidation reaction zone wherein the hydrogen chloride is contacted with a molten salt mixture containing the higher and lower valent chlorides of a multivalent metal and oxygen to recover chlorine by enriching the higher valent metal chloride content of the molten salt, said oxidation reaction zone being operated at a pressure of from 1 to 20 atm and a molten salt inlet temperature of from 750° F. to 950° F., said oxidation reaction zone being operated at a pressure which is at least 0.5 atm. greater than the dechlorination zone of step (d) and the molten salt inlet temperature to the oxidation reaction zone being at least 50° F. less than the molten salt inlet temperature to the dechlorination zone of step (d);
   (d) passing molten salt from the oxidation reaction zone to a dechlorination zone wherein the molten salt is contacted with a stripping gas which is inert with respect to the molten salt and which is inert with respect to the chlorination, said dechlorination zone being operated at a pressure of from 0.1 to 3.0 atm. and a molten salt inlet temperature of from 850° F. to 1000° F. to strip chlorine from the molten salt;
   (e) recovering gaseous chlorine from the dechlorination zone; and
   (f) passing recovered gaseous chlorine to the chlorination zone.

8. The process of claim 7 wherein the gaseous chlorine and stripping gas recovered from the dechlorination zone are introduced into the chlorination zone.

9. The process of claim 8 wherein the gaseous chlorine and stripping gas withdrawn from the dechlorination zone are essentially free of water.

10. The process of claim 9 wherein the stripping gas employed in the dechlorination zone is a portion of the hydrogen chloride recovered from the effluent from the chlorination zone.

11. The process of claim 8 wherein the gaseous chlorine and stripping gas recovered from the dechlorination zone contains from 5 to 40 mole percent chlorine.

12. The process of claim 11 wherein the molten salt mixture contains a mixture of cuprous and cupric chloride.

13. The process of claim 11 wherein the molten salt introduced into the dechlorination zone is free of water and the oxide of the multivalent metal.

* * * * *